United States Patent [19]

Woodward

[11] Patent Number: 5,775,896
[45] Date of Patent: Jul. 7, 1998

[54] VERSATILE OPERATORY LIGHT SYSTEM

[75] Inventor: Gary W. Woodward, Vancouver, Wash.

[73] Assignee: Micron Dental Manufacturing, Inc., Missouls, Mont.

[21] Appl. No.: 401,717

[22] Filed: Mar. 10, 1995

[51] Int. Cl.[6] ............................................. A61C 1/00
[52] U.S. Cl. ................................................. 433/29
[58] Field of Search ........................... 433/29, 98, 126; 600/178, 182; 323/267, 911

[56] References Cited

U.S. PATENT DOCUMENTS

| | | | |
|---|---|---|---|
| 3,634,938 | 1/1972 | Hutchinson | 433/29 |
| 4,477,252 | 10/1984 | Lieb et al. | 433/29 |
| 5,267,857 | 12/1993 | Sickler | 433/29 |

FOREIGN PATENT DOCUMENTS 1280339  7/1972  United Kingdom ............ 433/29

*Primary Examiner*—Cary E. O'Connor
*Attorney, Agent, or Firm*—Trask, Britt & Rossa

[57] ABSTRACT

A low voltage power supply includes a plurality of output terminal pairs interconnected by electrical circuitry effective to permit individual adjustment of the voltages applied between each such pair for powering simultaneously a plurality of light sources at individually selected voltages. The light sources are associated with dental handpieces through umbilical tubings, an exemplary one of which includes a bundle of flexible, light-conducting fibers connected between a first coupling fixture holding a subminiature bulb and a second coupling structurally adapted for connection to a dental handpiece.

21 Claims, 5 Drawing Sheets

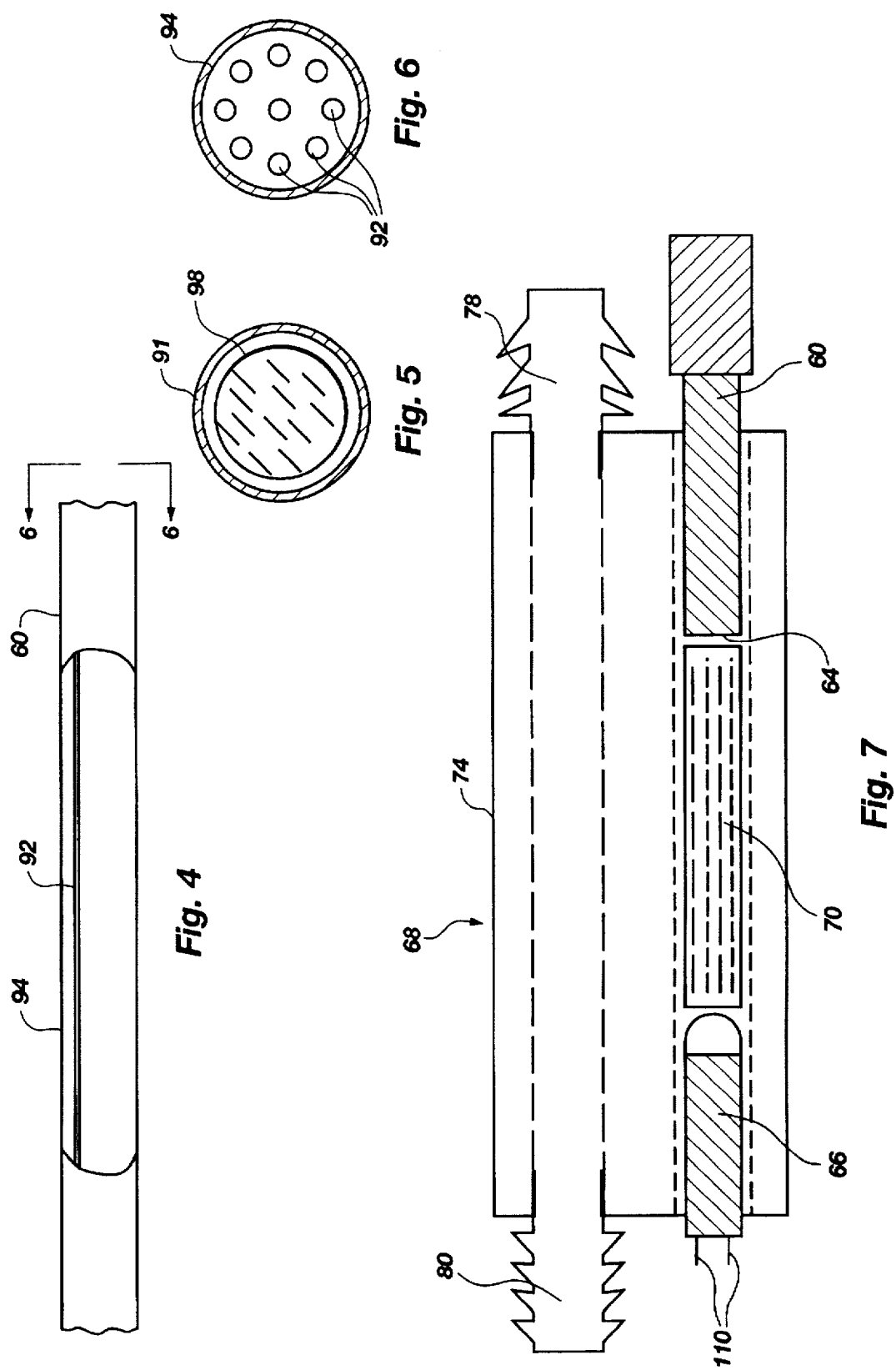

VERSATILE OPERATORY LIGHT SYSTEM

BACKGROUND

1. Field

This invention pertains to operatory lighting systems, particularly such systems for illuminating the oral cavity of a dental patient. It is particularly directed to a versatile system which provides both hard wired and fiber optic illumination capabilities for dental handpieces.

2. State of the Art

Modern dental offices are conventionally equipped with hand held devices called "handpieces." A handpiece, most typically an air-driven dental drill, is connected to its drive air supply through a conduit system comprising a portion of a utility bundle. The bundle is usually contained within a long flexible umbilical casing, often called a "hose," or "handpiece tubing," and conventionally includes passageways to accommodate drive air, exhaust air, chip air, water and lighting for the handpiece. U.S. Pat. Nos. 4,334,863; 4,553,938; 4,975,058; 5,088,924 and 5,145,370 describe representative conventional handpiece tubing assemblies of this type.

Lighting has been provided to handpieces by two distinct approaches. According to one approach, a fiber optic bundle is connected at a proximal end to a light generator and at a distal end to a handpiece. The fiber bundle is positioned within the umbilical utility hose (handpiece tubing). The fiber bundles used commercially for this purpose originally comprised glass fibers, although more recently, other light-transmitting fibers, notably acrylic fibers, have been proposed. An alternative arrangement, sometimes called the "power optic" system, positions a high intensity subminiaturized light bulb at the distal end of the umbilical hose. Power is delivered to the bulb through wires strung down the umbilical hose for connection to a power supply. This approach is best illustrated by U.S. Pat. No. 4,334,863.

A major inconvenience in the field has been the incompatibility of components of the fiber optic and power optic systems generally. Fiber optic systems conventionally utilize high intensity "projector" bulbs operated at standard house voltage, e.g. 120 volts. Power optic systems require a low voltage power generator dissimilar from those available in fiber optic systems. Moreover, the power generators furnished by any particular manufacturer have been incompatible with the bulbs associated with the handpiece tubings of the power optic systems supplied by other such manufacturers. Current major suppliers of power optic systems utilize subminiature bulbs which operate at 3.5 volts, 4.09 volts and 5.5–6 volts, respectively. These bulbs each require suitably matched power supplies. Accordingly, once a selected power optic system is acquired, and the appropriate power supply is installed in the field, the purchaser has limited options with respect to replacement parts or upgrades to the system.

Recently, adjustable power supplies for power optic installations have become available. The output voltage of these devices may be adjusted for use with a selected bulb voltage. Once adjusted, however, a single output voltage is available for use. Accordingly, the installation is limited as a practical matter to interfacing with the handpiece tubings of a single selected power optic system. Under current conditions, it remains necessary to provide a plurality of distinct power supplies in association with a dental operatory to support the operation of handpiece tubings furnished by a corresponding plurality of original equipment suppliers.

U.S. Pat. Nos. 4,957,347; 5,052,778 and 5,067,831 together disclose linear optical conduits, and their disclosures are instructive concerning the state of the art with respect to fiber optic technology generally. Among other things, these patents disclose various embodiments of a flexible, clad, monofilament optical conduit constructed around a flexible, light-transmitting, polymeric core characterized by a relatively high refractive index. The core is surrounded by a shrunk, heat shrinkable cladding, which has a relatively low refractive index compared to that of the core. The disclosures of U.S. Pat. Nos. 4,957,347; 5,052,778 and 5,067,831 are incorporated into this disclosure by reference for their teachings of materials and structures which may be incorporated into certain preferred embodiments of this invention.

SUMMARY OF THE INVENTION

This invention provides a low voltage power supply capable of functioning as the power source for a plurality of handpieces connected through power optic handpiece tubings currently extant in the field. It also provides a unique fiber optic handpiece tubing constructed and arranged to incorporate a subminiature low voltage bulb as the light source; thereby avoiding the need for the conventional high voltage power supply and projector bulb. Individual terminals of the power supply provide regulated voltage at appropriate levels; e.g., 3.5, 4 and 6 volts, to drive, either individually or simultaneously, all of the power optic handpiece tubings currently ubiquitous in the field. The same power supply may be utilized to drive the fiber optic handpiece tubings of this invention.

The novel fiber optic handpiece tubings of this invention preferably comprise a unique acrylic optical bundle. The bundle assembly desirably includes an input tip capable of withstanding the temperatures associated with existing fiber optic light generators and subminiature krypton, halide bulbs; i.e., as high as about 500° F. The acrylic bundle contains fewer strands of larger diameter and is of significantly less weight than conventional glass fiber optic bundles. Its use thus offers the advantages of reduced operator hand fatigue and increased resistance to fiber breakage. Moreover, the acrylic material filters out the undesirable brown, yellow and green portions of the light spectrum passed by typical glass fiber bundles.

The acrylic fiber bundles of this invention may be incorporated into a dental handpiece tubing of the type disclosed by U.S. Pat. Nos. 4,975,058; 5,088,924 and 5,145,370, for example. The input tip can then be associated with a high energy, low voltage, subminiature bulb, connected via a wiring harness to a remote power supply and control circuitry. This capability frees fiber optic operatory lighting from its traditional association with long bundle lengths anchored at one end to a light generator.

The disclosures of U.S. Pat. Nos. 4,334,863; 4,553,938; 4,975,058; 5,088,924 and 5,145,370 are incorporated by reference for their descriptions of handpieces and other components relevant to the systems of this invention. It is contemplated that monofilament optical conduits of the type disclosed by the aforementioned U.S. Pat. Nos. 4,957,347; 5,052,778 and 5,067,831, even if constructed with a core material other than a cured acrylic resinous material, will constitute a highly preferred light conduit for use in the practice of this invention.

As used in this disclosure and the appended claims: the term "high voltage" refers to voltages above about 50 volts, more typically normal house voltages of 120/240 volts nominal; "low voltage" refers to voltages below about 50 volts, more typically below about 10 volts, generally an order of magnitude below "high voltage;" and "subminiature bulbs" refers to incandescent, typically halide or krypton/halide, low voltage bulbs having diameters of less than about ⅛ inch (30 millimeters). While these specific values are not themselves critical, they are currently regarded as embracing the practical range for this invention, and as distinguishing the components of this invention from other devices which would be unsuitable for use within the context of this disclosure. The term "light source" refers generically to bulbs utilized as the source for light delivered by any means through or in connection with a handpiece tubing to a dental handpiece.

The invention may be regarded as comprising two distinct but intercooperable advances in the art; namely a novel, low voltage fiber optic handpiece tubing arrangement, and a specialized multi-output, variable low voltage power supply capable of powering multiple subminiature bulbs.

A notable component of the preferred embodiments of this invention is a novel system for conducting light to a dental handpiece. The system comprises a bundle of flexible, light-conducting fibers directly associated with a subminiature bulb. The bundle has a first end structured to terminate in a window capable of receiving light from the bulb, and a second end capable of emitting light conducted by the bundle from its first end. A first coupling fixture associated with the first end of the bundle is structured and arranged to hold a subminiature bulb within the fixture juxtaposed with respect to the window when the first end of the bundle is inserted within the first coupling. A second coupling fixture is associated with the second end of the bundle, and is structurally adapted for connection to a dental handpiece. When so attached, illumination is furnished through the handpiece in generally conventional fashion. Of course, the bundle generally comprises a handpiece tubing arrangement.

The first coupling fixture ideally includes a heat-conducting body with a longitudinal axis and a first longitudinal passage approximately parallel that axis. This first longitudinal passage will have a proximal end, closest to the power source, and a distal end, closest to the fiber bundle. The proximal end is structurally configured to receive and contain a subminiature bulb. The distal end is structurally configured to receive the first end of the bundle. A heat-insulating, light-transmitting plug, such as a length of glass rod, may be positioned within the first longitudinal passage to occupy a portion of that passage between a bulb-receiving portion of the proximal end of the passage and a bundle-receiving portion of the distal end of the passage. Other embodiments include a second longitudinal passage through the heat-conducting body, approximately parallel the first longitudinal passage. The second longitudinal passage is provided with barbed fixtures at an inlet end and an outlet end to accommodate the flow of cooling fluid, typically air, through the second longitudinal passage. The complete system includes a low voltage power supply connected to power a subminiature bulb associated with the first coupling fixture.

A power supply of this invention includes a plurality of output terminal pairs electrically connected to a power source through circuitry constructed and arranged to permit individual adjustment of the voltage applied between the terminals of each such pair. The circuit constitutes means for powering simultaneously a plurality of light sources at individually selected voltages. A useful such power supply generally includes a housing; a plurality of output terminal pairs mounted to the housing; a power source associated with the housing; and electrical circuitry interconnecting the terminal pairs with the power source. The circuitry is constructed and arranged to permit individual adjustment of the voltage applied between the terminals of each terminal pair. In this fashion, the power supply is enabled to provide power simultaneously to a plurality of light sources at individually selected voltages. The power supply may be installed in combination with a plurality of dental handpiece tubings, each such tubing carrying a low voltage light source, and each such light source being connected to a selected terminal pair.

BRIEF DESCRIPTION OF THE DRAWINGS

In the drawings, which illustrate what is currently regarded as the best mode for carrying out the invention.

FIG. 4 is an enlarged fragment of the assembly of FIG. 3, taken from the region 4—4 of FIG. 3;

FIG. 5 is a view in elevation, taken from the reference line 5—5 of FIG. 3;

FIG. 6 is a view in cross section, taken along the reference line 6—6 of FIG. 3;

FIG. 7 is a pictorial view, partially in section, of a preferred optical coupler of this invention;

DESCRIPTION OF THE ILLUSTRATED EMBODIMENTS

Figure 1:
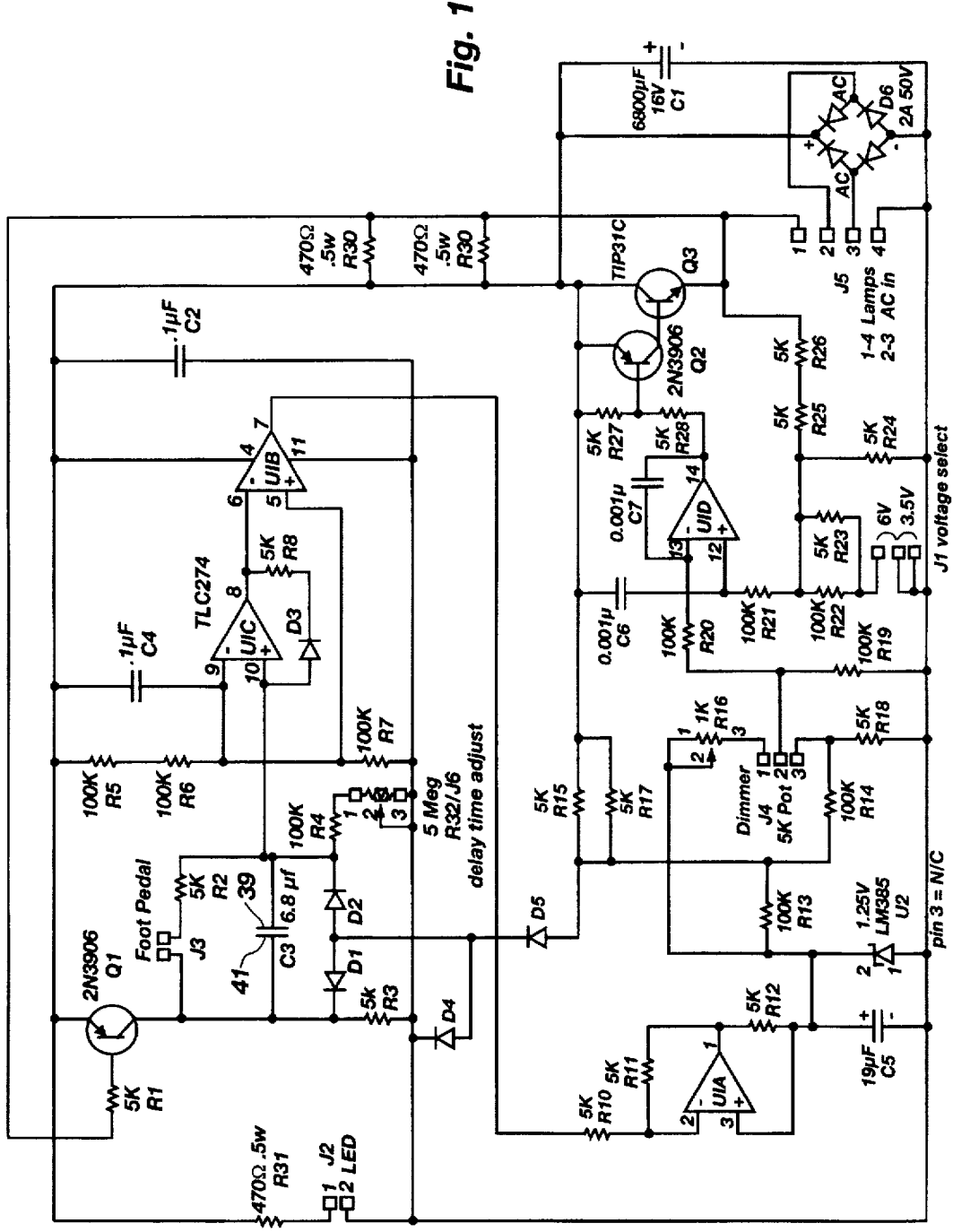
FIG. 1 is a schematic diagram of a simple version of the power supply of this invention.
Figure 2:
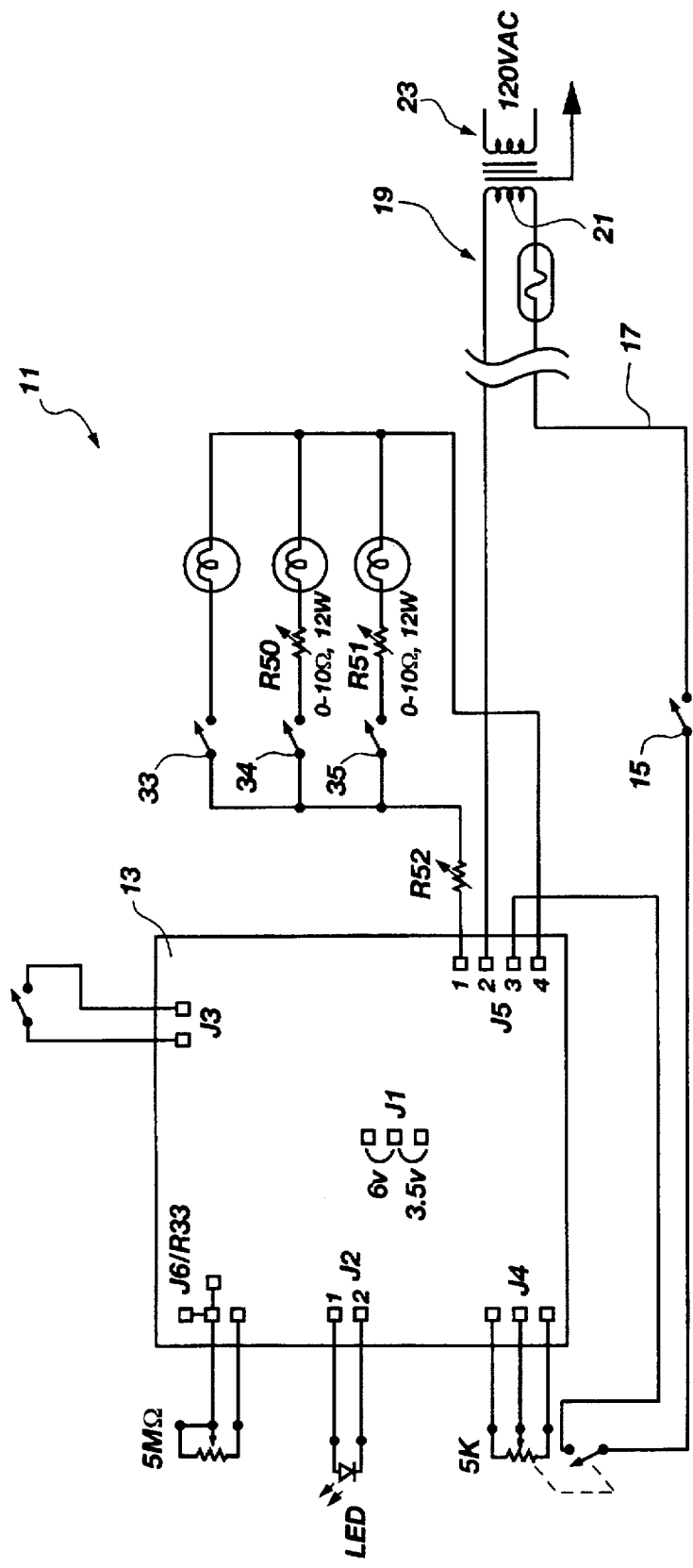
FIG. 2 is a schematic diagram of a system incorporating the power supply of FIG. 1.
Figures 8, 9:
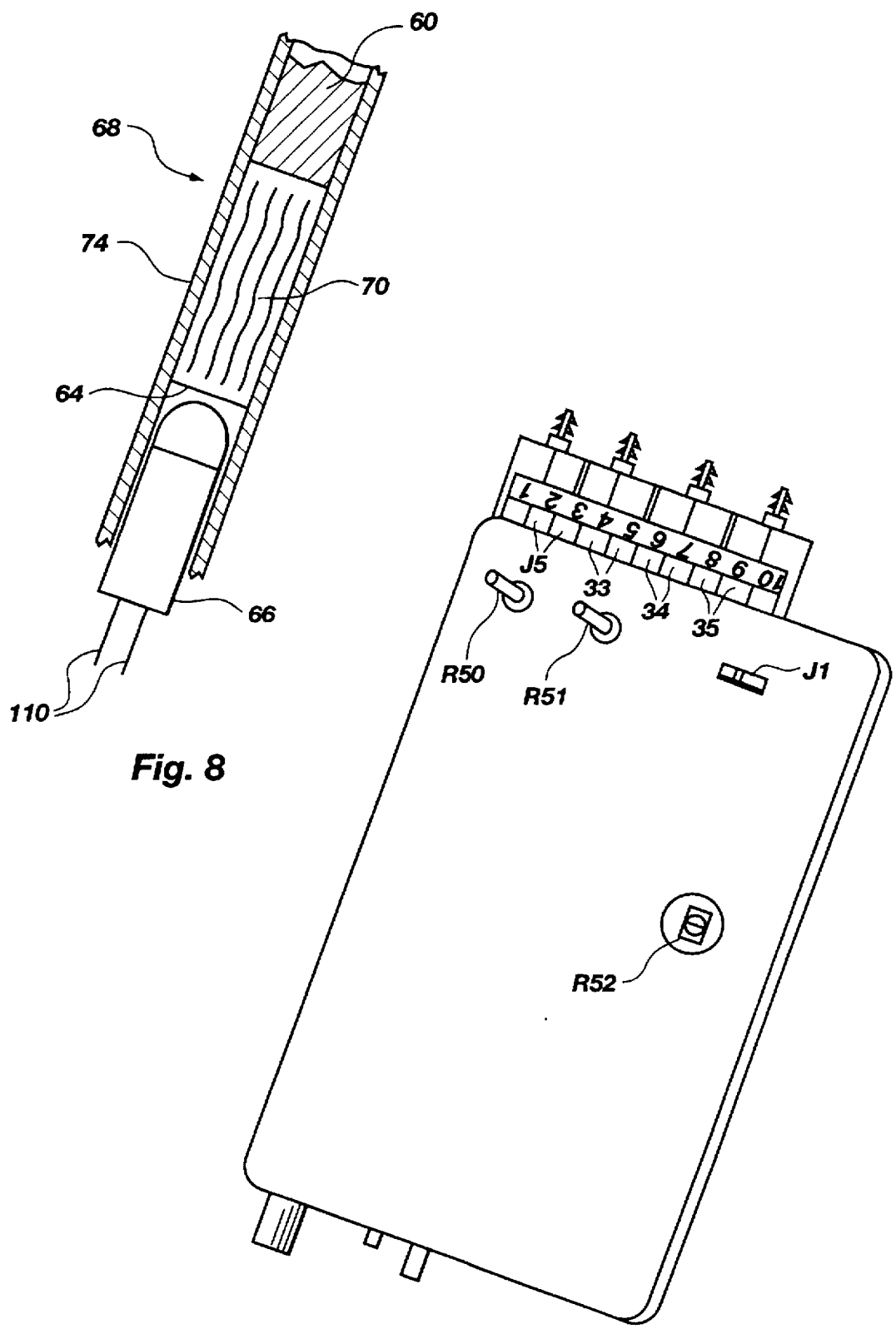
FIG. 8 is a view in section of an alternative optical coupler of this invention.
FIG. 9 is a pictorial view of an assembled power supply of this invention.

As illustrated by FIGS. 1, 2 and 9, a light controller, generally 11, includes a circuit board 13 associated with voltage selection terminals, J1, LED display, J2, a foot pedal air switch, J3, a dimmer control, J4, handpiece holder switch circuits, J5, an optional time adjustment, J6, and a master air switch 15 in the fused conductor 17 of a power cord 19 leading from the low voltage side 21 of a power transformer 23.

Figure 3:
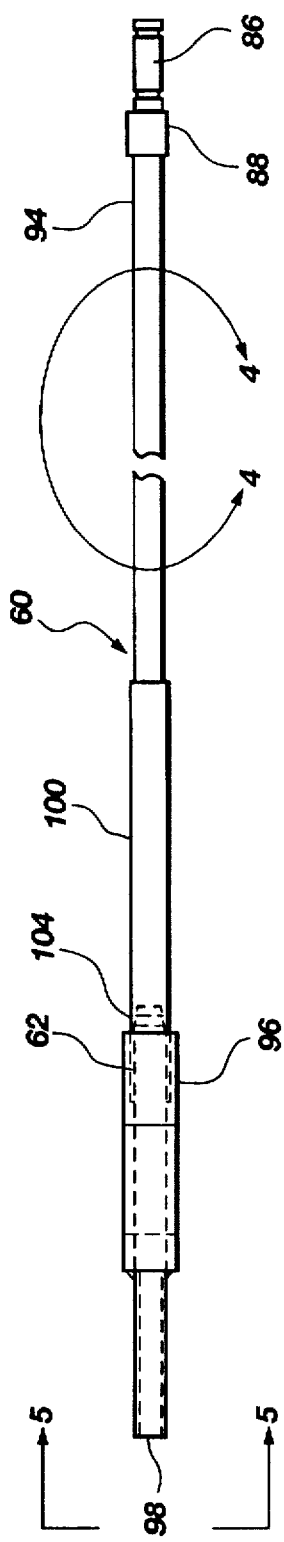
FIG. 3 is a pictorial view of a fiber optic bundle assembly of this invention.

Practical components of the circuit board 13 are shown by FIGS. 1, 3.5 or 6 volt DC power is selected at J1, and is supplied to 720 ma incandescent lamps at J5. The timer at J6 turns on for an adjustable 1–35 second period when a handpiece is removed from a holder to activate a switch 33, 34, 35 (FIG. 2) at J5. The timer remains on for so long as the foot switch at J3 is closed and remains on for a delay of 1–35 seconds after the switch is again opened. With a handpiece out of its holder, a quiescent voltage (typically 5–10% of its normal operating voltage) is applied across the lamp to enhance its useful life. An approximately 1.5 volt reference drop across diodes D4 and D5 is fed across the resistors R13 and R14 to provide this bias voltage. The illustrated circuit also functions through operational amplifier U1A and capacitor C5 to increase the applied voltage gradually over a fraction (typically 0.3) of a second when a lamp is energized.

Power is applied to pins 2 and 3 of J5 at about 5 or 7 volts AC. It is rectified by the diode bridge D6 and filtered by capacitor C1. Operational amplifier UID and transistors Q2 and Q3 comprise a regulator for the incoming voltage to insure application of the proper lamp voltages at J1. Reference diode U2 provides, through the dimmer potentiometer R16, a reference voltage for the regulator. The lamp voltage is thus maintained at 3 or 5.13 times the voltage detected at pin 2 at J4. R16 may be adjusted to effect a maximum dimmer output of 1.167 volts, thereby setting the maximum J1 terminal voltages at 3.5 and 6 volts, respectively. Operational amplifier U1B inverts the on/off signal from the timer output at J6. Operational amplifier U1C functions as a comparator for the timer circuit. When a lamp is on, both sides of the timer capacitor C3 are at high potential. As the capacitor C3 charges through timing resistors R4 and R32, the potential at one side 39 of the capacitor C3 falls below the level set by resistors R5, R6 and R7. The output of amplifier U1C then becomes low, causing a high output from amplifier U1B, shutting off the bias current to diode U2. The output potential at J1 then shuts off, except for the quiescent voltage across resistors R13 and R14.

When all handpieces are in their holders, there is no load across the regulator output. This output thus floats up to match the incoming supply voltage, thereby turning off transistor Q1. The potential on the side 41 of capacitor C3 then reduces. Diode D2 prevents the potential applied to the side 39 of capacitor C3 from reducing to below the negative supply voltage. When a handpiece is removed from a holder, the regulator output voltage returns to its quiescent level, thereby turning on transistor Q1 to raise the potential at 41. Because the capacitor C3 is discharged, the potential at 39 also increases, turning on the reference voltage biases to the opertional amplifiers U1A, U1B and U1C.

If it is desired to operate only 3.5 volt bulbs, the appropriate selection is made at J1 at the time the power supply is installed. The voltage applied between pins 1 and 4 of J5 is then 3.5 volts. Power resistors R50 and R51 remain set at approximately zero ohms resistance, and the voltage applied at each of the lamp switches 33, 34 and 35 remains at 3.5 volts. The voltage at each of these switches may be adjusted to 6 volts at J1. Assuming that the voltage selected at J1 is 6 volts, the voltage applied at each of the switches 33, 34 and 35 my be adjusted to a lesser common voltage, e.g. 4 volts, by adjustment of variable resistor R52. Power resistors R50 and R51 may be individually adjusted to provide reduced voltages at switches 34 and 35. It is thus possible to provide power for three different handpiece tubing assemblies, each operating at any selected voltage up to about 6 volts. In the event it becomes desirable to provide different handpiece tubings at the operatory subsequent to the initial installation, the existing power supply can be adjusted in the field, rather than replaced.

The illustrated power supply is suitable for operation of the fiber optic handpiece tubing of this invention through any of the switches 33, 34 and 35 adjusted to provide appropriate output voltage. The bulbs currently preferred for the illustrated embodiments have a focal point of approximately 1/10 inch, and require approximately 6 volts for optimum operation.

A preferred fiber optic assembly of this invention is best shown by FIGS. 3–6, while its manner of coupling to a low voltage light source is illustrated by FIGS. 7 and 8. The bundle, generally 60, illustrated is an acrylic bundle of the type disclosed in U.S. Pat. Nos. 4,975,058; 5,088,924 and 5,145,370, and may be provided in any convenient length, typical standard lengths being between about 6 and about 14 feet. Acrylic bundles comprising between 1 and 64 fibers are currently regarded as useful for this invention. The diameters of the individual fibers in a bundle will be dependant upon their total number and the diameter of the bundle. An exemplary bundle 60 incorporates 19 strands of 0.020 inch diameter acrylic fibers bonded within an end fitting 62 with clear R.T.V. resin. A more flexible bundle utilizes a greater number of smaller diameter fibers. The terminus 64 of the fitting is polished to constitute an entry window to receive light from a bulb 66 (FIGS. 7 and 8). The optical coupler 68 positions a short, typically about 1 to about 2 inches of a clear insulating material, typically glass rod 70, between the bulb 66 and the fiber bundle 60. The glass rod illustrated is capable of withstanding temperatures as high as 500° F. These components are contained within a heat conductive casing, such as the aluminum block 74 shown. FIG. 7 illustrates a coupling arrangement which provides for cooling air circulating through a passage in the aluminum block 74 between first 78 and second 80 tubing connectors. Either connector, 78, 80, may function as the air inlet, depending upon whether drive or exhaust air is circulated through the block 74. In the embodiments illustrated by either of FIGS. 7 or 8, the insulating rod 70 may be fixed in place, thereby avoiding the need to fabricate fiber bundles which individually incorporate these components.

A conventional grooved proto tip 86 (FIG. 3) at the output end 88 of the bundle 60 connects to a handpiece in conventional fashion. Referring to FIGS. 4–6, the fibers 92 of the bundle 60 are positioned within a siliconized polyurethane sheathing 94, which is fastened to a rod holder 96 swaged to a clad rod end tip 98. A length 100 of shrink tubing protects the source end 104 of the bundle 60 from damage which could result from severe bending.

It should be recognized that the optical bundle illustrated by FIG. 3 may be appreciably shorter that the handpiece tubing within which it is contained. The wires 110 illustrated in FIGS. 7 and 8 may be of any convenient length, and the optical couplers 68 may be located at any desired position between the power supply 11 and output end 88 of the bundle 60.

Reference to specific details of the illustrated embodiments is not intended to restrict the scope of the appended claims. These claims recite those details regarded as significant to the invention, and are intended to include within their scope all equivalents adduceable by one skilled in the art from this disclosure.

What is claimed is:

1. A system for conducting light to a dental handpiece, said system comprising:

a bundle of flexible, light-conducting fibers, said bundle having a first end structured to terminate in a window capable of receiving light from a light source and a second end capable of emitting light conducted by said bundle from said first end;

a first coupling fixture associated with said first end structured and arranged to hold a subminiature bulb within said first coupling fixture juxtaposed with respect to said window when said first end is inserted within said first coupling;

a second coupling fixture associated with said second end and structurally adapted for connection to a dental handpiece, whereby to furnish illumination through said handpiece; and a subminiature bulb mounted within said first coupling fixture.

2. A system according to claim 1, wherein said bundle comprises a handpiece tubing arrangement.

3. A system according to claim 1, including a low voltage power supply connected to power a subminiature bulb associated with said first coupling fixture.

4. A system according to claim 3, wherein said power supply includes a plurality of output terminal pairs electrically connected to a power source through circuitry constructed and arranged to permit individual adjustment of the voltage applied between the terminals of each said pair, whereby to provide means for powering simultaneously a plurality of light sources at individually selected voltages.

5. A system for conducting light to a dental handpiece, said system comprising:
   a bundle of flexible, light-conducting fibers, said bundle having a first end structured to terminate in a window capable of receiving light from a light source and a second end capable of emitting light conducted by said bundle from said first end;
   a first coupling fixture associated with said first end structured and arranged to hold a subminiature bulb within said first coupling fixture juxtaposed with respect to said window when said first end is inserted within said first coupling:
   a second coupling fixture associated with said second end and structurally adapted for connection to a dental handpiece, whereby to furnish illumination through said handpiece;
   wherein said first coupling fixture includes a heat-conducting body with a longitudinal axis and a first longitudinal passage approximately parallel said axis, said first longitudinal passage having a proximal end and a distal end, said proximal end being structurally configured to receive and contain a subminiature bulb and said distal end being structurally configured to receive said first end of said bundle.

6. A system according to claim 5, including a heat-insulating, light-transmitting plug within said first longitudinal passage, occupying a portion of said first longitudinal passage between a bulb-receiving portion of said proximal end and a bundle-receiving portion of said distal end.

7. A system according to claim 5, including a second longitudinal passage through said body, approximately parallel said first longitudinal passage, said second longitudinal passage having an inlet end and an outlet end, whereby to accommodate the flow of cooling fluid through said second longitudinal passage.

8. A system for conducting light to a dental handpiece, said system comprising:
   a bundle of flexible, light-conducting fibers, said bundle having a first end structured to terminate in a window capable of receiving light from a light source and second end capable of emitting light conducted by said bundle from said end:
   a first coupling fixture associated with said first end structured and arranged to hold a subminiature bulb within said first coupling fixture juxtaposed with respect to said window when said first end is inserted within said first coupling; and
   a second coupling fixture associated with said second end and structurally adapted for connection to a dental handpiece, whereby to furnish illumination through said handpiece:
   further including a low voltage power supply connected to power a subminiature bulb associated with said first coupling fixture wherein said first coupling fixture includes a heat-conducting body with a longitudinal axis and a first longitudinal passage approximately parallel said axis, said first longitudinal passage having a proximal end and a distal end, said proximal end being structurally configured to receive and contain said subminiature bulb and said distal end being structurally configured to receive said first end of said bundle.

9. A low voltage power supply, comprising:
   a housing:
   a plurality of output terminal pairs mounted to said housing:
   a power source associated with said housing: and
   electrical circuitry interconnecting said terminal pairs with said power source, said circuitry being constructed and arranged to permit individual adjustment of the voltage applied between the terminals of each said pair, whereby to provide means for powering simultaneously a plurality of light sources at individually selected voltages;
   in combination with a plurality of dental handpiece tubings each such tubing carrying a low voltage light source, and each such light source being connected to a selected said terminal pair:
   wherein at least one of said handpiece tubings comprises a system including:
   a bundle of flexible, light-conducting fibers, said bundle having a first end structured to terminate in a window capable of receiving light from a light source and a second end capable of emitting light conducted by said bundle from said first end.

10. A combination according to claim 9, wherein said system further comprises:
    a first coupling fixture associated with said first end structured and arranged to hold a subminiature bulb within said coupling juxtaposed with respect to said window when said first end is inserted within said first coupling; and
    a second coupling fixture associated with said second end and structurally adapted for connection to a dental handpiece, whereby to furnish illumination through said handpiece.

11. A combination according to claim 10, wherein said first coupling fixture includes a heat-conducting body with a longitudinal axis and a first longitudinal passage approximately parallel said axis, said first longitudinal passage having a proximal end and a distal end, said proximal end being structurally configured to receive and contain a subminiature bulb and said distal end being structurally configured to receive said first end of said bundle.

12. A combination according to claim 11, including a heat-insulating, light-transmitting plug within said first longitudinal passage, occupying a portion of said first longitudinal passage between a bulb-receiving portion of said proximal end and a bundle-receiving portion of said distal end.

13. A combination according to claim 11, including a second longitudinal passage through said body, approximately parallel said first longitudinal passage, said second longitudinal passage having an inlet end and an outlet end, whereby to accommodate the flow of cooling fluid through said second longitudinal passage.

14. A combination according to claim 10, wherein said first coupling is associated with a dental handpiece tubing and is positioned remote from said power supply.

15. In combination:
    a system for conducting light from a light source to a dental handpiece, said system comprising:
    a bundle of flexible, light-conducting fibers, said bundle having a first end structured to terminate in a window capable of receiving light from said light source and a second end capable of emitting light conducted by said bundle from said first end;

a first coupling fixture associated with said first end structured and arranged to hold a subminiature bulb within said coupling juxtaposed with respect to said window when said first end is inserted within said first coupling;

a second coupling fixture associated with said second end and structurally adapted for connection to a dental handpiece, whereby to furnish illumination through said handpiece;

a subminiature bulb mounted within said first coupling fixture; and a low voltage power supply connected to power said subminiature bulb.

16. A combination according to claim 15, wherein said bundle comprises a handpiece tubing arrangement.

17. A combination according to claim 15, wherein said first coupling fixture includes a heat-conducting body with a longitudinal axis and a first longitudinal passage approximately parallel said axis, said first longitudinal passage having a proximal end and a distal end, said proximal end being structurally configured to receive and contain a subminiature bulb and said distal end being structurally configured to receive said first end of said bundle.

18. A combination according to claim 17, including a heat-insulating, light-transmitting plug within said first longitudinal passage, occupying a portion of said first longitudinal passage between a bulb-receiving portion of said proximal end and a bundle-receiving portion of said distal end.

19. A combination according to claim 17, including a second longitudinal passage through said body, approximately parallel said first longitudinal passage, said second longitudinal passage having an inlet end and an outlet end, whereby to accommodate the flow of cooling fluid through said second longitudinal passage.

20. A combination according to claim 15, wherein said power supply includes a plurality of output terminal pairs electrically connected to a power source through circuitry constructed and arranged to permit individual adjustment of the voltage applied between the terminals of each said pair, whereby to provide means for powering simultaneously a plurality of light sources at individually selected voltages.

21. A combination according to claim 20, wherein said first coupling fixture includes a heat-conducting body with a longitudinal axis and a first longitudinal passage approximately parallel said axis, said first longitudinal passage having a proximal end and a distal end, said proximal end being structurally configured to receive and contain said subminiature bulb and said distal end being structurally configured to receive said first end of said bundle.

* * * * *